(12) United States Patent
Masters et al.

(10) Patent No.: US 8,397,762 B2
(45) Date of Patent: Mar. 19, 2013

(54) FLUIDIC SYSTEM WITH IMPROVED FLOW CHARACTERISTICS

(75) Inventors: Brett P. Masters, Belmont, CA (US); Peter Wight Falb, Hingham, MA (US); Michael F. Miller, Hollis, NH (US)

(73) Assignee: BioScale, Inc., Cambridge, MA (US)

( * ) Notice: Subject to any disclaimer, the term of this patent is extended or adjusted under 35 U.S.C. 154(b) by 0 days.

(21) Appl. No.: 12/025,385

(22) Filed: Feb. 4, 2008

(65) Prior Publication Data

US 2009/0194181 A1 Aug. 6, 2009

(51) Int. Cl.
*F15C 1/04* (2006.01)

(52) U.S. Cl. ............ 137/827; 137/833; 73/861.18; 422/559

(58) Field of Classification Search .......... 137/807, 137/827, 828, 825, 803, 833; 73/861.18, 73/861.21, 861.08; 422/505, 559
See application file for complete search history.

(56) References Cited

U.S. PATENT DOCUMENTS

| | | | |
|---|---|---|---|
| 3,285,263 A * | 11/1966 | Bjornsen et al. ............. 137/825 |
| 5,189,914 A | 3/1993 | White et al. ................. 73/599 |
| 5,411,709 A | 5/1995 | Furuki et al. ................ 422/91 |
| 5,744,367 A | 4/1998 | Talley et al. ................. 436/172 |
| 5,763,191 A | 6/1998 | Knoll et al. .................. 435/7.1 |
| 5,955,729 A | 9/1999 | Nelson et al. ................ 250/282 |
| 5,965,456 A | 10/1999 | Malmqvist et al. ........... 436/514 |
| 6,200,814 B1 | 3/2001 | Malmqvist et al. ........... 436/52 |
| 6,454,924 B2 | 9/2002 | Jedrzejewski et al. ........ 204/601 |
| 6,551,836 B1 | 4/2003 | Chow et al. .................. 436/149 |
| 6,558,944 B1 | 5/2003 | Parce et al. .................. 435/287.2 |
| 6,676,835 B2 * | 1/2004 | O'Connor et al. ............ 137/833 |
| 6,698,454 B2 | 3/2004 | Sjölander et al. ............ 137/885 |
| 6,823,895 B2 * | 11/2004 | Hitchcock et al. ........... 137/827 |
| 7,118,922 B1 | 10/2006 | Bhansali et al. ............. 436/518 |
| 7,300,631 B2 | 11/2007 | Miller et al. ................ 422/82.01 |
| 7,410,811 B2 | 8/2008 | Lin et al. .................... 436/526 |
| 2002/0115198 A1 | 8/2002 | Nerenberg et al. .......... 435/287.2 |
| 2003/0010745 A1 | 1/2003 | Field ............................ 216/2 |
| 2003/0022388 A1 | 1/2003 | Roos et al. ................... 436/164 |
| 2003/0134431 A1 | 7/2003 | Parce et al. .................. 436/518 |

(Continued)

FOREIGN PATENT DOCUMENTS

| | | |
|---|---|---|
| DE | 102 41 099 | 6/2004 |
| EP | 1752663 | 2/2007 |

(Continued)

OTHER PUBLICATIONS

Grate, et al., "Acoustic Wave Sensors," Sensors Update, 1996, pp. 37-83.

(Continued)

*Primary Examiner* — Craig Schneider
*Assistant Examiner* — Craig J Price
(74) *Attorney, Agent, or Firm* — Proskauer Rose LLP

(57) ABSTRACT

The invention relates to a fluidic system that includes a body structure having a chamber disposed therein. The fluidic system includes at least one fluid input at a first end of the chamber and at least one fluid output at a second end of the chamber. The fluidic system also includes a sensor device (e.g., an acoustic device) having a surface defining a portion of a surface of the chamber. The fluidic system also includes a first surface at the first end of the chamber oriented at an oblique or arcuate (e.g., curved) angle relative to the surface of the sensor device to direct fluid through the chamber.

11 Claims, 4 Drawing Sheets

U.S. PATENT DOCUMENTS

| | | | | |
|---|---|---|---|---|
| 2003/0154031 | A1 | 8/2003 | Potyrailo et al. | 702/19 |
| 2003/0201022 | A1* | 10/2003 | Kawai et al. | 137/828 |
| 2004/0016297 | A1 | 1/2004 | Paul et al. | 73/580 |
| 2004/0043423 | A1 | 3/2004 | Bellew et al. | 435/7.1 |
| 2004/0211251 | A1* | 10/2004 | Lee et al. | 73/146.3 |
| 2005/0040907 | A1 | 2/2005 | Nebrigic | 332/118 |
| 2006/0137434 | A1* | 6/2006 | Cohen et al. | 73/61.43 |
| 2007/0000327 | A1 | 1/2007 | Sung et al. | 73/584 |
| 2007/0117214 | A1 | 5/2007 | Masters et al. | 436/149 |
| 2008/0115599 | A1 | 5/2008 | Masters et al. | 73/866 |

FOREIGN PATENT DOCUMENTS

| | | |
|---|---|---|
| WO | WO 2005/111426 | 11/2005 |
| WO | 2006/119308 | 11/2006 |

OTHER PUBLICATIONS

Padmanabhan et al., "A Wafer-Bonded Floating-Element Shear Stress Microsensor with Optical Position Sensing by Photodiodes", Journal of Microelectromechanical Systems, Dec. 1996, vol. 5, No. 4, pp. 307-315.

Wang, et al., "A Silicon-based Ultrasonic Immunoassay for Detection of Breast Cancer Antigens", Sensors and Actuators, vol. 49 (1998), pp. 13-21.

Armani et al., "Re-Configurable Fluid Circuits by PDMS Elastomer Micromachining", Proceedings of the IEEE Electro Mechanical Systems, Orlando, FL, Jan. 1999, pp. 222-227.

Kanai et al., "PDMS Microfluidic Devices with PTFE Passivated Channels", 7th International Conference on Miniaturized Chemical and Biochemical Analysis Systems (Oct. 5-9, 2003), pp. 429-432.

Lettieri et al., "A Novel Microfluidic Concept for Bioanalysis Using Freely Moving Beads Trapped in Recirculating Flows", Lab Chip, 2003, vol. 3, pp. 34-39.

Cunningham et. al, "Design, Fabrication and Vapor Characterization of a Microfabricated Flexural Plate Resonator Sensor and Application to Integrated Sensor Arrays", Sensors and Actuators B, vol. 73, (2001) pp. 112-123.

Choi et al., "Development and Characterization of Microfluidic Devices and Systems for Magnetic Bead-Based Biochemical Detection", Biomedical Microdevices, vol. 3:3, (2001) pp. 191-200.

Jensen, "Microreaction Engineering—Is Small Better?", Chemical Engineering Science, vol. 56 (2001), 293-303.

Choi et. al., "A New Magnetic Bead-Based, Filterless Bio-Separator with Planar Electromagnet Surfaces for Integrated Bio-Detection Systems", Sensors and Actuators B, vol. 68 (2000), pp. 34-39.

Cowan et al., "Ultrasonic Flexural-Plate-Wave Sensor for Detecting the Concentration of Settling *E. coli* W3110 Cells", Anal. Chem., (1999), vol. 71, pp. 3622-3625.

Höök et al., "Energy Dissipation Kinetics for Protein and Antibody-Antigen Adsorption under Shear Oscillation on a Quartz Crystal Microbalance", Langmuir (1998), vol. 14, pp. 729-734.

Fredriksson et al., "The Piezoelectric Quartz Crystal Mass and Dissipation Sensor: A Means of Studying Cell Adhesion", Langmuir (1998), vol. 14, pp. 248-251.

Wang et al., "A Silicon-based Ultrasonic Immunoassay for Detection of Breast Cancer Antigens", International Conference on Solid State Sensors and Actuators, Transducers '97, vol. 1, Chicago, IL, Jun. 16-19, 1997, pp. 191-194.

Black et al., "Microsphere Capture and Perfusion in Microchannels Using Flexural Plate Wave Structures", IEEE Ultrasonics Symposium, (2002) pp. 475-479.

Costello et al., "A Flexural-Plate-Wave Microbial Sensor", IEEE (1992) 0-7803-0456-X92, pp. 69-72.

\* cited by examiner

FLUIDIC SYSTEM WITH IMPROVED FLOW CHARACTERISTICS

TECHNICAL FIELD

The invention relates to fluidic systems with fluid chambers having improved fluid flow characteristics.

BACKGROUND

As the size of electromechanical, electro-optical, and electronic fluidic systems shrink to micrometer and nanometer scales, components within those systems necessarily shrink as well. Smaller components require more precise processing techniques to ensure optimal system performance. Operation of the fluidic systems is extremely sensitive to the fluid flow characteristics within the system and, in particular, at locations in the fluidic system where sensor measurements are conducted.

In particular, fluidic systems that use acoustic devices (e.g., flexural plate wave devices) are very sensitive to flow characteristics of the fluid flowing through the fluidic system. Typical acoustic devices include surface acoustic wave devices, flexural plate wave devices, lamb wave devices and cantilever devices. Signals output by acoustic devices are typically monitored to determine properties (e.g., density and viscosity) of the fluid or, for example, the amount and/or number of biomolecular targets in the fluid sample that have bound to a surface of the acoustic device.

Acoustic devices couple to fluids predominantly through acoustic interaction between the acoustic device and the fluid. Acoustic devices also couple to fluids through some viscous interaction between the acoustic device and the fluid, however, the coupling is predominantly acoustic coupling. Viscous interaction devices couple to fluids predominantly through viscous interaction between the devices and the fluid. Typical viscous interaction devices include quartz microbalance (QCM) devices, shear harmonic surface acoustic wave devices, and acoustic plate mode devices. The term "surface acoustic wave" refers to the manner in which energy is carried in the device structure rather than how the device couples to the fluid. Acoustic devices are devices where fluid interacts over a substantial area of a plane of the device. Acoustic devices respond with substantial out of plane motion that couples acoustically to fluid in proximity to the plane of the device (i.e., kinetic energy, potential energy and losses are carried substantially in the fluid). Viscous interaction devices respond primarily with in-plane motion that does not couple acoustically to fluid in proximity to a plane of the device.

Because acoustic devices interact with the fluid, they are particularly sensitive to irregularities or variations in the fluid flow characteristics. Inadequately designed fluidic systems have poor macroscopic performance and lead to loss of sensitivity, accuracy and/or repeatability. These issues can be particularly important in systems used to detect or measure biomolecular targets in fluid samples.

Hence there is a need for fluidic systems and sensor devices in which uniform, repeatable flows are produced in the fluidic system and, in particular, in sensing regions of the fluidic systems.

SUMMARY

The invention, in one aspect, features a fluidic system that includes a body structure having a chamber disposed therein. The fluidic system also includes at least one fluid input at a first end of the chamber and at least one fluid output at a second end of the chamber. The fluidic system also includes a sensor device (e.g., an acoustic device) having a surface defining a portion of a surface of the chamber. The fluidic system also includes a first surface at the first end of the chamber oriented at an oblique or arcuate (e.g., curved) angle relative to the surface of the sensor device to direct fluid through the chamber.

In some embodiments, the fluidic system includes a second surface at the second end of the chamber oriented at an oblique angle to the surface of the sensor device to direct fluid out of the chamber. In some embodiments, the first surface at the first end of the chamber is configured to transition fluid flow direction from a first direction to a second perpendicular direction. In some embodiments, the second surface at the second end of the chamber is configured to transition fluid flow direction from the second perpendicular direction to a third direction.

In some embodiments, the fluidic systems includes an input chamber coupled to the at least one fluid input at the first end of the chamber, the input chamber cross-sectional area decreasing as it approaches the at least one fluid input. In some embodiments, the fluidic system includes an output chamber coupled to the at least one fluid output at the second end of the chamber, the output chamber cross-sectional area increasing further away from the at least one fluid output.

In some embodiments, the fluidic system includes one or more additional surfaces located at the first end of the chamber oriented at oblique or arcuate angles relative to the surface of the sensor device to direct fluid through the chamber. In some embodiments, the fluidic system also includes a removable source of magnetic flux located external to the chamber and adjacent the sensor surface. In some embodiments, a projection of at least one of the fluid input or fluid output on to a plane defined by the surface of the sensor device does not overlap with the surface of the sensor device.

The invention, in another aspect, features a method for improving fluid flow characteristics in a fluidic system. The method involves directing a fluid flow into a fluid input at a first end of a chamber in a fluidic system. The method also involves directing the fluid flow to impinge on a first oblique or arcuate angled surface at the first end of the chamber, altering the direction of the fluid flow to produce uniform fluid flow characteristics across a surface of a sensor device defining at least a portion of the surface of the chamber.

In some embodiments, the method involves creating a magnetic flux close to the surface of the sensor device to attract magnetic particles in the fluid to the surface of the sensor device. In some embodiments, the method involves selectively altering the magnetic flux close to the surface of the sensor device. In some embodiments, the method involves altering at least one of fluid pressure, flow rate or flow volume.

The details of one or more examples are set forth in the accompanying drawings and the description below. Further features, aspects, and advantages of the invention will become apparent from the description, the drawings, and the claims.

DETAILED DESCRIPTION

Figure 1:
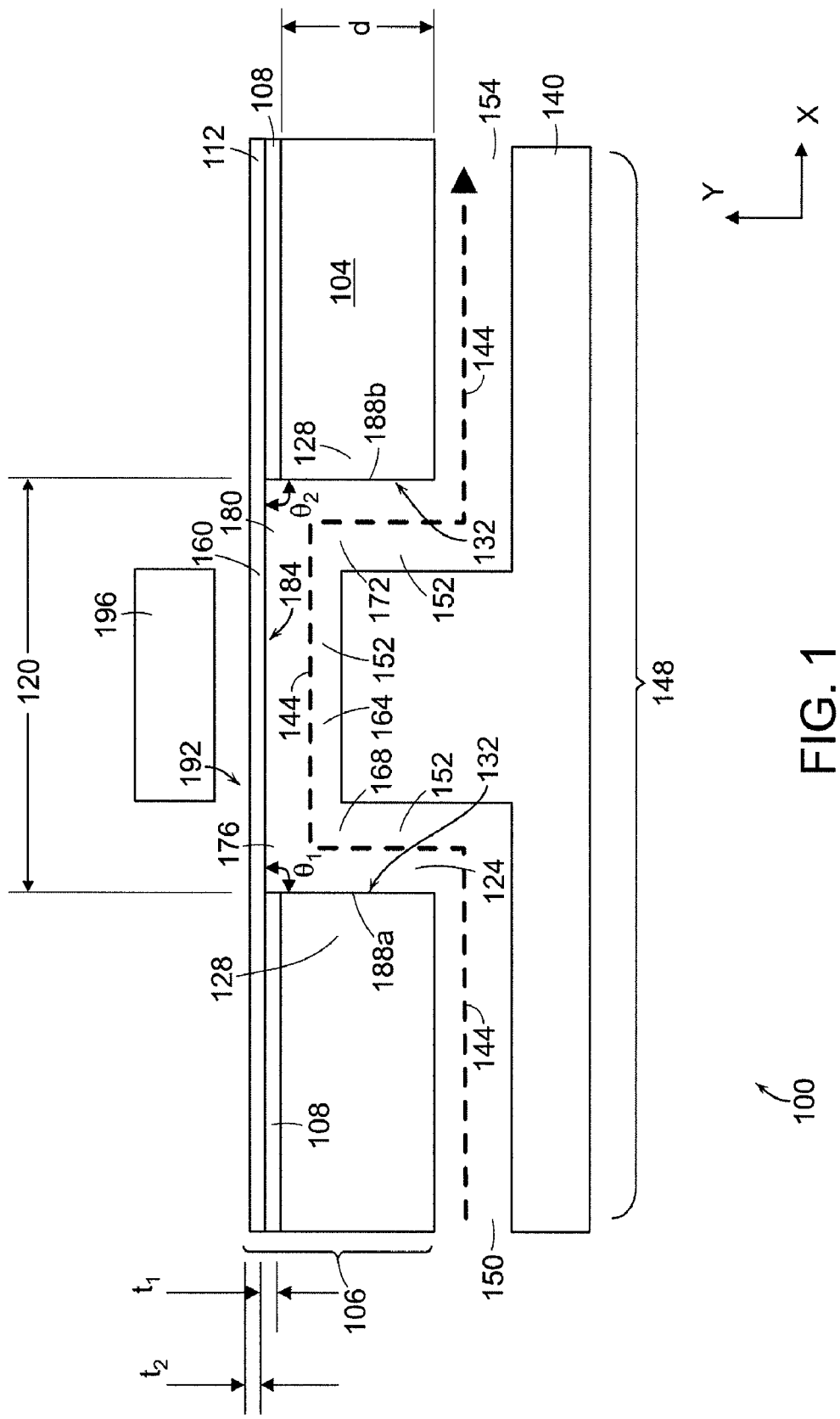
FIG. 1 is a cross-sectional schematic view of a prior art fluidic system.

FIG. 1 is a cross-sectional schematic view of a prior art fluidic system 100. The fluidic system 100 includes a cartridge 148 having a body structure (not shown) that includes a wafer 106 and a base 140. The wafer 106 includes a sensor device 160 (e.g., an acoustic device) that is a suspended membrane. The wafer 106 has a cavity 152. The wafer 106 and base 140, in combination, define a fluid chamber 164 and a fluid path 144. The fluid chamber 164 has a fluid input 168 at a first end 176 of the chamber 164. The fluid chamber 164 also has a fluid output at a second end 180 of the chamber 164.

Fluid flows in to the cartridge 148 via a first input 150. The fluid flows along the positive X-axis direction of the fluid path 144. The fluid then changes direction and flows along the positive Y-axis direction of the fluid path 144. The fluid then flows through the fluid input 168 at the first end of 176 of the fluid chamber 164. The fluid flow then changes direction and flows along the positive X-axis direction towards the second end 180 of the fluid chamber 164. Fluid in the chamber 164 interacts with the sensor device 160 of the chamber 164. The sensor device 160 outputs a signal based on the interaction of the fluid with the sensor device 160.

Magnetic particles in the fluid are attracted by a removable source of magnetic flux 196 (external to the chamber 164) to a surface 184 of the sensor device 160. The source of magnetic flux 196 can be, for example, a rare earth magnet. The source of magnetic flux 196 is positioned close to the sensor device 160 to create a magnetic flux close to the surface 184 of the sensor device 160 to attract the magnetic particles (and substances bound to the magnetic particles) to the surface 184 of the sensor device 160. In some embodiments, the magnetic flux is selectively altered. In some embodiments, altering the magnetic flux alters the distribution (e.g., improves the distribution) of the magnetic particles on the surface 184 of the sensor device 160.

At the second end 180 of the fluid chamber 164, the fluid flow changes direction and flows along the fluid path 144 in the negative Y-Axis direction. Fluid flows through the fluid output 172 at the second end 180 of the fluid chamber 164. The fluid flow then changes direction and flows along the fluid path 144 along the positive X-Axis direction. Fluid then flows out of a first output 154 of the cartridge 148 where it can be, for example, disposed.

In some embodiments, fluid flow properties are altered using one or more flow control devices (e.g., pumps, syringes or valves) to alter at least one of fluid pressure, flow rate or flow volume in the fluidic system. In some embodiments, altering fluid flow properties improves, for example, sensor device repeatability, insures that surfaces in the fluidic system are adequately wetted, or reduces gas bubbles in the fluidic system.

The wafer 106 includes a substrate material 104, an intermediate layer 108 disposed on the substrate material 104, and a membrane layer 112 disposed on the intermediate layer 108. In general, the substrate 104 is a material that can be etched. Examples of suitable substrate materials include, for example, silicon, glasses, dielectric materials, metals, or materials suitable for laser micromachining. Semiconductor processing equipment and methods can be used to create different features (e.g., fluid paths) in the fluidic system 100.

The size of the opening 120 along the X-axis and the Z-axis (not shown) can be between about 10 micrometers and about 10,000 micrometers depending on the particular application for the wafer 100. In some fluidic systems, the size of the opening 120 is also the length (in the X-Axis direction) of the sensor device 160. In some fluidic systems, the length of the sensor device 160 is less than the size of the opening 120 and the surface 184 of the sensor device 160 defines a portion of the chamber 164 wall. In some fluidic systems, the opening 120 is rectangular in shape. The opening 120 can also have circular, elliptical, or irregular geometry. In some fluidic systems, the wafer 106 is subjected to a dry removal process to produce a chamber 124. The chamber 124 includes walls 128 defined by the substrate material 104 which are exposed after the dry removal process.

The dry removal process can involve, for example, a deep reactive ion etching process ("DRIE" process). Deep reactive ion etching is a highly anisotropic etch that is used to create relatively high-aspect ratio holes (e.g., cavities with substantially vertical walls 128 relative to the y-axis). In this fluidic system, portion 188a of the fluidic system 100 is oriented at an angle $\theta_1$ that is substantially perpendicular to the surface 184 of the sensor device 160. In addition, portion 188b of the fluidic system 100 is oriented at an angle $\theta_2$ that is substantially perpendicular to the surface 184 of the sensor device 160

Deep reactive ion etching generally involves either cryogenic wafer processing or the "Bosch process," both of which are known to those of skill in the art. An advantage of deep reactive ion etching processes includes improved control over the geometry of a relatively deep chamber 124 (e.g., a chamber having a depth d greater than about 100 micrometers). Improved control over the geometry of the chamber 124 results from the deep reactive ion etching process involving a sequence of alternating etching and passivating steps. In some fluidic systems, the intermediate layer 108 is an etch stop layer. The etch stop layer prevents the dry removal process from contacting or otherwise removing material from the membrane 112. For example, the intermediate layer 108 can be formed of a material that is not susceptible to removal by the dry removal process. The material properties of the intermediate layer 108 prevent the dry removal process from removing material from the membrane 112 even if the intermediate layer 108 is not an etch stop layer, but is merely a sacrificial layer.

The depth d of the chamber is measured along the Y-axis in a direction normal to the intermediate layer 108, the membrane 112, or both. In some fluidic systems, the depth d of the chamber is between about 100 micrometers and about 1,000 micrometers, depending on the particular application for the wafer 106. For example, the phase velocity or group velocity of a traveling wave on the sensor device 160 of the membrane 112 and interacting with the fluid can be influenced by the dimensions of the chamber 124. In addition, the wavelength or period of the wave can be influenced by boundary conditions imposed by the chamber 124, the intermediate layer 108, and/or the membrane 112. In this embodiment, the depth d of the chamber is relatively large (compared to, for example, the thickness $t_2$ along the Y-axis of the membrane 112). To achieve a relatively large depth d, removal processes with a relatively high etch rate and a relatively high selectivity to the surrounding structures are preferred.

In fluidic systems including an intermediate layer 108, the intermediate layer 108 defines a first thickness $t_1$ of between about 0.1 and about 10 micrometers measured along the Y-axis. The thickness $t_1$ of the intermediate layer 108 may be selected based on a thickness (not shown) of a layer of fluid that interacts with the sensor device 160 of the membrane 112 during operation.

In this fluidic system, the dry removal process involves an etching process. Etching can involve removal with a chemical etchant, with a laser, or by ion bombardment. The dry removal process can also include ablation techniques, for example, vaporization, chipping, or other erosive processes. In this fluidic system, the dry removal process includes an isotropic etching process. In general, isotropic etching involves directionally-independent removal of a portion of the substrate material 104 using, for example, a chemical substance. More particularly, isotropic etchants attack a material in all directions at substantially the same rate.

In some fluidic systems, the dry removal process includes an alternating sequence of etching and passivation. A portion of the substrate 104 is removed during the etching step with an etchant (not shown). The etchant is then removed, and a passivating substance (not shown) is provided to the portion of the substrate remaining after etching. The passivating substance (e.g., a polymer or polymer residue) serves to protect the portion of the surface 132 of the wall 128, that has already been etched, from being further etched by the etchant as the depth of the chamber (along the Y-axis) is increased with subsequent etchings. In this way, the geometry of the chamber 124 (e.g., the walls 128 and angle of the walls relative to the intermediate layer 108) can be more accurately controlled.

The cavity 152 depth (along the Y-Axis) is defined by an intermediate layer 108 that separates the membrane layer 112 from the substrate 104. The material that forms this intermediate layer 108 is chosen to be resistant to the etching process used to define the cavity 152. An example of a suitable etch stop material is silicon dioxide (SiO2) when the substrate 104 is a silicon material and a dry removal process such as deep reactive ion etching is used to form the cavity 152. After the cavity 152 is formed, the etch stop layer may be removed. For example, a silicon dioxide layer can be removed from the surface of the membrane layer 112 using hydrofluoric acid. In some cases, a diluted or buffered form of hydrofluoric acid is used. Dry removal processes are also available for removing oxide layers.

An exemplary description of wafer processing to create a fluidic system is described below to illustrate the types of devices that can employ features of the concepts described herein. In some fluidic systems, additional microfabrication process steps can be performed on the membrane 112, and the membrane 112 is sometimes considered to be a device layer. Layers can be added to the membrane 112 using techniques such as physical or chemical vapor deposition, sputtering, bonding, ion implantation, molecular beam epitaxy, or other methods. These layers can be patterned using standard photolithographic techniques that involve masking layers and etching steps. For example, the membrane 112 can be a p-type semiconductor material, having a resistivity of 4-6 ohm-centimeters and a thickness $t_2$ of about 2.2 micrometers. The top surface 192 of the membrane 112 can be modified by implantation of boron atoms (not shown). For example, a dose of about $5 \times 10^{15}/cm^2$ with energy of about 35 keV can be performed followed by rapid thermal annealing at about 1,100° C. for about 30 seconds. In other embodiments, a highly doped layer of silicon can be deposited onto the membrane 112. In other embodiments a metal layer can be deposited onto the membrane 112.

In some embodiments, reactive sputtering is used to deposit an electroactive layer or film (not shown), (e.g., a piezoelectric material such as aluminum nitride), on the doped membrane 112. An oxide mask (e.g., silicon dioxide) (not shown) can be deposited on the electroactive layer using, for example, chemical vapor deposition. The mask can be patterned with a photoresist material (not shown) and etched with a buffered hydrofluoric acid to form an outline of a via (not shown) to the membrane 112. The via is etched using hot phosphoric acid, and the oxide mask is stripped from the wafer 100 using buffered hydrofluoric acid. The via can be used for electrical communication with the membrane 112 (e.g., for providing an electrical signal in actuating applications or for measuring an electrical signal in sensing applications).

In some fluidic systems, a metal layer (not shown) is deposited on the electroactive layer (not shown). In some fluidic systems, two or more metals are deposited. In fluidic systems having two metals, the first metal is titanium having a thickness of about 0.02 micrometers, and the second metal is gold having a thickness of about 0.08 micrometers. The metals form electrodes on the surface of the electroactive layer. The metals are patterned and etched to form, for example, interdigitated electrodes according to a desired design to produce an acoustic device capable of actuating the electroactive layer and capable of sensing changes in the resonant response of the composite membrane 112. The acoustic device is capable of, for example, outputting a signal that varies based on changes in physical properties of a fluid that is in contact with a surface of the resonant device. A protectant, for example, a photoresist material (not shown) can be deposited over processed surface (not shown) of the membrane 112 to protect the membrane layers from being affected by subsequent removal processes (e.g., similarly as discussed above for forming the chamber 124). In some fluidic systems, any of the above steps can be employed to form a device layer on the membrane 112.

Figure 2:
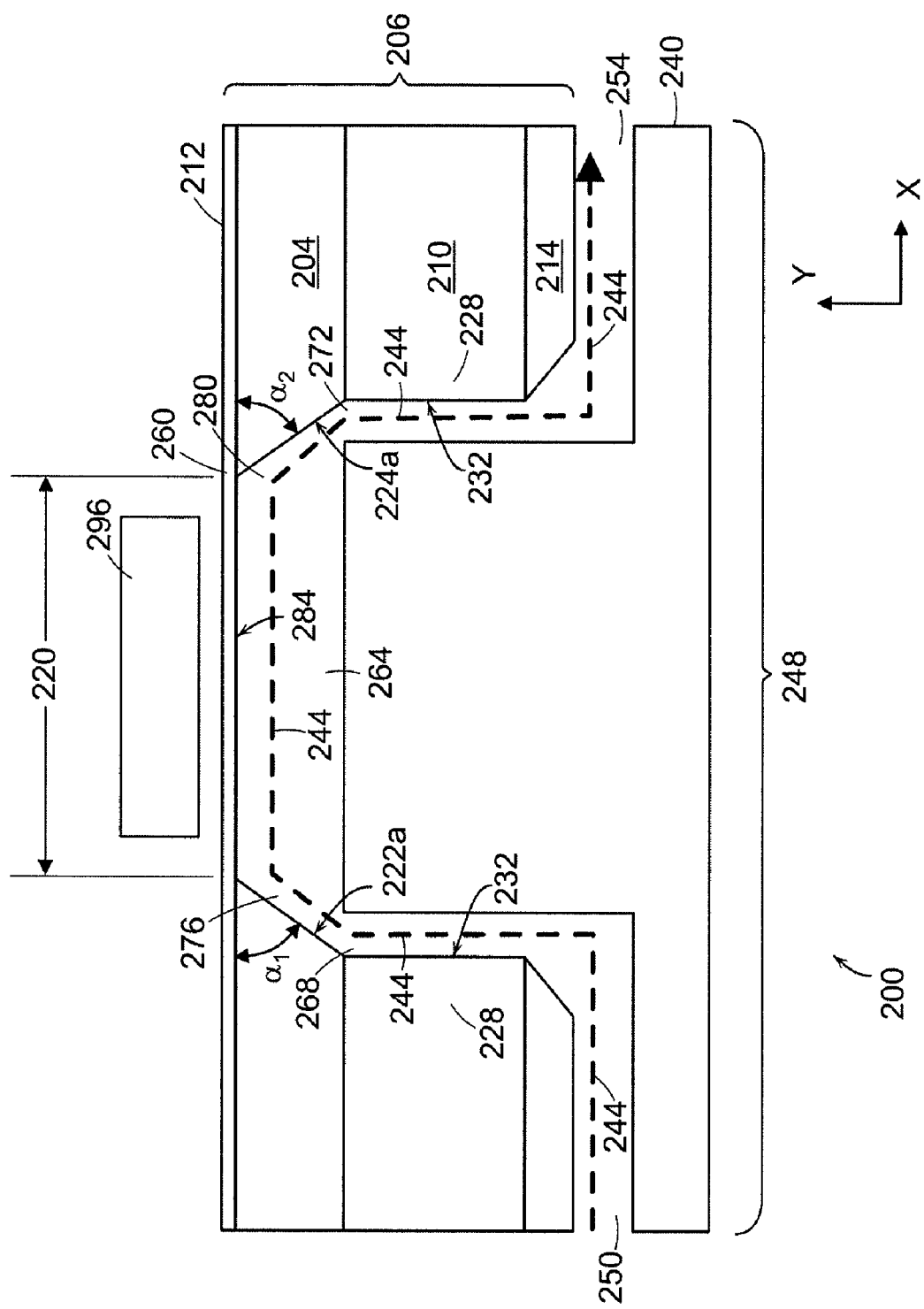
FIG. 2 is a cross-sectional schematic view of a fluidic system, according to an illustrative embodiment of the invention.

FIG. 2 is a cross-sectional schematic view of a fluidic system 200, according to an illustrative embodiment of the invention. The fluidic system 200 includes a cartridge 248 having a body structure (not shown) that includes a wafer 206 and a base 240. The wafer 206 has a sensor device 260 that is a suspended membrane. In some embodiments, the length 220 is the length of one wall of the chamber 264 (opposite the removable source of magnetic flux 296) and also is the length of the sensor device 260 (in the X-Axis direction). In some fluidic systems, the length of the sensor device 260 is less than the length 220 and the surface 284 of the sensor device 260 defines a portion of a surface of the chamber 264 wall. The wafer 206 and base 240, in combination, define a fluid chamber 264 and a fluid path 244. The fluid chamber 264 has a fluid input 268 at a first end 276 of the chamber 264. The fluid chamber 264 has a fluid output 272 at a second end 280 of the chamber 264.

Fluid flows in to the cartridge 248 via a first input 250. The fluid flows along the positive X-axis direction of the fluid path 244. The fluid then changes direction and flows along the positive Y-axis direction of the fluid path 244. The fluid then flows through the fluid input 268 at the first end of 276 of the fluid chamber 264.

The fluidic system 200 has a surface 222a at the first end 276 of the fluid chamber 264. The surface 222a is oriented at an angle $\alpha_1$ relative to a surface 284 of the sensor device 260. The angled orientation of the surface 222a relative to the surface 284 of the sensor device 260 causes fluid flow to change from a first flow direction (substantially in the positive Y-Axis direction) to a second flow direction in the chamber 264 (substantially in the positive X-Axis direction). Because the surface 222a changes causes the flow to change from the first flow direction to the second flow direction, the flow (e.g., direction and velocity of the flow) is more uniform across the surface 284 of the sensor device 260 in the chamber 264 than the flow would otherwise be in the absence of the surface 222a (e.g., flow across the surface 184 of the sensor device 160 in FIG. 1 is less uniform). In addition, in some embodiments, flow direction and velocity is more uniform near the center of the sensor device 260 (in both the Y-Axis and X-Axis) than at the edges of the sensor device 260 because turbulence or irregularity in the flow due to a change in the flow direction has had sufficient time to decrease or subside. In this embodiment, the first flow direction is substantially perpendicular to the second flow direction.

In this embodiment, the surface 222a is oriented at an oblique angle (i.e., an angle that is not a right angle or a multiple of a right angle). In some embodiments, the surface 222a is a curved surface and the surface 222a is oriented at an arcuate angle relative to the surface 284 of the sensor device 260. In some embodiments, one or more additional surfaces are located at the first end 276 of the fluid chamber 264. The one or more additional surfaces are each located at oblique or arcuate angles relative to the surface 284 of the sensor device 260. The one or more additional surfaces are configured to cause fluid flow to change from the first flow direction (substantially in the positive Y-Axis direction) to the second flow direction in the chamber 264 (substantially in the positive X-Axis direction).

Fluid in the chamber 264 interacts with the sensor device 260 of the chamber 264. The sensor device 260 outputs a signal based on the interaction of the fluid with the sensor device 260. Magnetic particles in the fluid are attracted by a removable source of magnetic flux 296 to the surface 284 of the sensor device 260. The source of magnetic flux 296 can be, for example, a rare earth magnet. The source of magnetic flux 296 is positioned close to the sensor device 260 to create a magnetic flux close to the surface 284 of the sensor device 260 to attract the magnetic particles (and substances bound to the magnetic particles) to the surface 284 of the sensor device 260. In some embodiments, the magnetic flux is selectively altered. In some embodiments, altering the magnetic flux alters the distribution (e.g., improves the distribution) of the magnetic particles on the surface 284 of the sensor device 260.

The fluidic system 200 has a surface 224a at the second end 280 of the fluid chamber 264. The surface 224a is oriented at an angle $\alpha_2$ relative to the surface 284 of the sensor device 260. The angled orientation of the surface 224a relative to the surface 284 of the sensor device 260 causes fluid flow to change from the second flow direction (substantially in the positive X-Axis direction) to a third flow direction (substantially in the negative Y-Axis direction). In this embodiment, the second flow direction is substantially perpendicular to the third flow direction.

In this embodiment, the surface 224a is oriented at an oblique angle (i.e., an angle that is not a right angle or a multiple of a right angle). In some embodiments, the surface 224a is a curved surface and, therefore, the surface 224a is oriented at an arcuate angle relative to the surface 284 of the sensor device 260.

Fluid flows through the fluid output 272 at the second end 280 of the fluid chamber 264. The fluid flow then changes direction and flows along the fluid path 244 along the positive X-Axis direction. Fluid then flows out of a first output 254 of the cartridge 248 where it can be, for example, disposed.

In some embodiments, fluid flow properties are altered using one or more flow control devices (e.g., pumps, syringes or valves) to alter at least one of fluid pressure, flow rate or flow volume in the fluidic system. In some embodiments, altering fluid flow properties improves, for example, sensor device repeatability, insures that surfaces in the fluidic system are adequately wetted, or reduces gas bubbles in the fluidic system.

The wafer 206 includes a substrate 204, a membrane material 212, a first material layer 210 and a second material layer 214. The first material layer 210 includes walls 228 having a substantially vertical surface 232 (walls 228 are substantially aligned along the Y-Axis). In some embodiments, the first material layer 210 and/or the second material layer 214 are the same material as the substrate 204. In some embodiments, the second material layer 214 is fabricated using a plastic material for cost and/or ease of manufacturing issues.

The membrane material 212 is deposited on the wafer 204 using, for example, thin-film deposition techniques such as chemical or physical vapor deposition techniques. The membrane material 212 can be, for example, a silicon nitride material. The silicon nitride material has advantageous properties when used as a membrane material 212 and for wafer processing. For example, silicon nitride can be deposited over the substrate 204. Silicon nitride, particularly low-stress variations of silicon nitride, works well as a membrane material and as an etch mask during formation of the chamber 264. A separate mask layer (not shown) is, therefore, not required to be deposited or patterned on the substrate 204 prior to formation of the chamber 264. The pattern can be formed directly in the silicon nitride material.

When the sensor device 260 membrane is formed from an electrically insulating material such as silicon nitride, a lower electrode layer is deposited on the sensor device 260 prior to depositing the piezoelectric and the upper electrode layers. Examples of suitable lower electrode materials are molybdenum or aluminum.

The surfaces 222a and 224a are oriented at angle $\alpha_1$ and angle $\alpha_2$, respectively, relative to the surface 284 of the sensor device 260 The angles $\alpha_1$ and $\alpha_2$ are determined based on the type of removal process used to form the chamber 264 and the type of substrate material 204 (e.g., the lattice structure of the substrate material 204). In this embodiment, an anisotropic etching process is used and the etchant is constrained by the crystal lattice structure of the substrate 204. For example, in one embodiment where the substrate is formed from single crystal silicon wafer, the angles $\alpha_1$ and $\alpha_2$ are 54.7° because the crystal lattice structure angle of the substrate is 54.7°. This geometry is achieved by using an anisotropic etchant, for example, potassium hydroxide.

In some embodiments, an intermediate layer (not shown) is located between the membrane material 212 and the substrate 204 and acts as an etch stop layer to prevent the removal processes that formed the chamber 264 from affecting the membrane material 212. In some embodiments, the intermediate layer is not an etch stop, but the membrane material 212 (e.g., silicon nitride) is resistant to the removal processes that form the chamber 264. In such embodiments, structural damage to the membrane material 212 is minimized because the membrane material 212 is resistant to, for example, the chemicals using during the removal process employed to create the chamber 264. This is particularly true when the membrane material 212 is silicon nitride and potassium hydroxide is used in a wet removal process to produce the chamber 264.

Figure 3A:
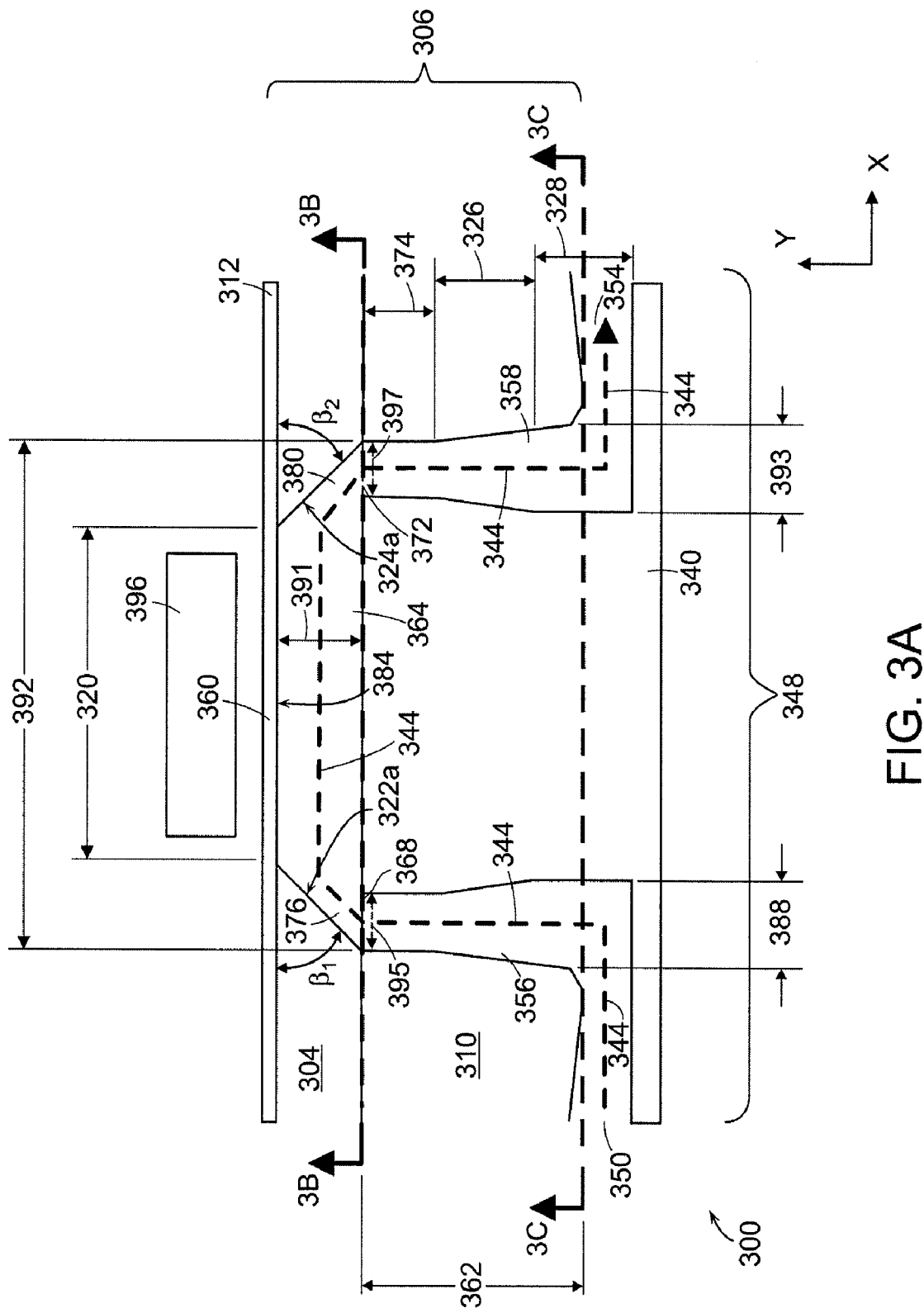
FIG. 3A is a cross-sectional schematic view of a fluidic system, according to an illustrative embodiment of the invention.
Figure 3B:
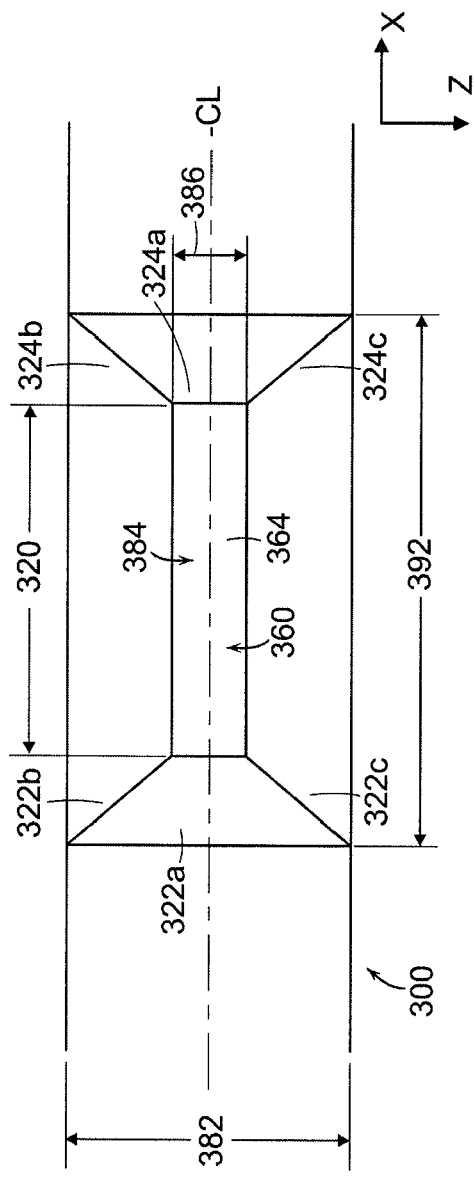
FIG. 3B is a cross-sectional perspective view of a portion of the fluidic system of FIG. 3A.
Figure 3C:
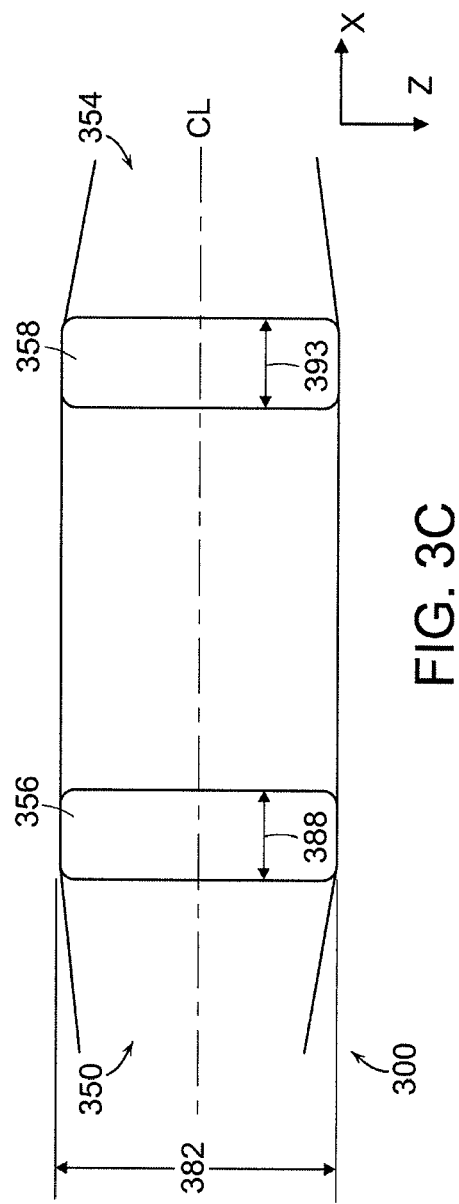
FIG. 3C is a cross-sectional view of the fluidic system of FIG. 3B.

FIGS. 3A, 3B and 3C are cross-sectional schematic views of a fluidic system 300, according to an illustrative embodiment of the invention. The fluidic system 300 includes a cartridge 348 having a body structure (not shown) that includes a wafer 306 and a base 340. The wafer 306 has a sensor device 360 that is a suspended membrane. In some embodiments, the length 320 is the length of one wall of the chamber 364 (opposite the removable source of magnetic flux 396) and also is the length of the sensor device 360 (in the X-Axis direction). In this embodiment, the length of the source of magnetic flux 396 along the X-Axis is less than the length 320. In alternative embodiments, the length of the source of magnetic flux 396 along the X-Axis is equal to the length 320. In some fluidic systems, the length of the sensor device 360 is less than the length 320 and the surface 384 of the sensor device 360 defines a portion of a surface of the chamber 364 wall. The wafer 306 and base 340, in combination, define a fluid chamber 364 and a fluid path 344. The fluid chamber 364 has a fluid input 368 at a first end 376 of the chamber 364. The fluid chamber 364 has a fluid output 372 at a second end 380 of the chamber 364.

Fluid flows in to the cartridge 348 via a first input 350. The fluid flows along the positive X-axis direction of the fluid path 344. The fluid then changes direction and flows along the positive Y-axis direction of the fluid path 344 in an input chamber 356 of the fluidic system 300. The input chamber 356 is in fluid communication with the fluid input 368 at the first end 376 of the chamber 364. The fluid input 368 has a width 395. The opening of the input chamber 356 (at the opposite end of the input chamber from the fluid input 368) has a width 388 and length 382.

The cross-sectional area of the input chamber 356 decreases as it approaches (in the positive Y-Axis direction) the fluid input 368. The input chamber 356 has a first section with a length 328 (along the Y-Axis) and width 388. The input chamber 356 has a second section with a length 326 (along the Y-Axis) and a width (along the X-Axis) that transitions from a width 388 to a width 395. The input chamber 356 has a third section with a length 374 (along the Y-Axis) with a width 395. The velocity of the fluid increases as it approaches the location of the fluid input 368 because of the decrease in cross-sectional area. The fluid then flows through the fluid input 368 at the first end of 376 of the fluid chamber 364. The fluid chamber 364 has a depth 391. In this embodiment, the width of the fluid input 368 and the width of the chamber 364 are nominally the same (width 382) to minimize disturbances to the fluid as it flows from the 356 into the chamber 364.

Referring to FIG. 3B, the fluidic system 300 has a first surface 322a, second surface 322b and third surface 322c at the first end 376 of the fluid chamber 364. The chamber 364 has a width 382 and length 392. The sensor device 360 has a width 386 and length 320. The first surface 322a, second surface 322b and third surface 322c are oriented at an angle $\beta_1$ relative to a surface 384 of the sensor device 360. The angled orientation of the first surface 322a, second surface 322b and third surface 322c relative to the surface 384 of the sensor device 360 causes fluid flow passing through the first opening 368 at the first end of the chamber 364 to change from a first flow direction (substantially in the positive Y-Axis direction) to a second flow direction in the chamber 364 (substantially in the positive X-axis direction). As shown in FIG. 3A, in some embodiments, the first opening 368 is arranged opposite the first surface 322a relative to the surface 384. Fluid flowing through the first opening 368 that is directed toward the second surface 322b and third surface 322c is directed toward the center line (CL) and along the second flow direction (substantially in the positive X-Axis direction). The velocity of the fluid increases when it is directed by the first surface 322a, second surface 322b and third surface 322c toward the center line. The fluid velocity increases because the cross-sectional area in the chamber is smaller at the surface 384 of the sensor device 360 than it is away from the surface 384 of the sensor device 360. In this embodiment, the first flow direction is substantially perpendicular to the second flow direction.

In this embodiment, the first surface 322a, second surface 322b and third surface 322c are oriented at an oblique angle (i.e., an angle that is not a right angle or a multiple of a right angle, and therefore is not perpendicular or substantially perpendicular with respect to the first surface, as shown in FIG. 3A). In some embodiments, the first surface 322a, second surface 322b and third surface 322c are curved surfaces and the first surface 322a, second surface 322b and third surface 322c are oriented at an arcuate angle relative to the surface 384 of the sensor device 360.

Referring to FIG. 3A, fluid in the chamber 364 interacts with the sensor device 360 of the chamber 364. The sensor device 360 outputs a signal based on the interaction of the fluid with the sensor device 360. Magnetic particles in the fluid are attracted by a removable source of magnetic flux 396 to the surface 384 of the sensor device 360. The source of magnetic flux can be, for example, a rare earth magnet or an electromagnet. The source of magnetic flux 396 is positioned close to the sensor device 360 to create a magnetic flux close to the surface 384 of the sensor device 360 to attract the magnetic particles (and substances bound to the magnetic particles) to the surface 384 of the sensor device 360. In some embodiments, the magnetic flux is selectively altered. In some embodiments, altering the magnetic flux alters the distribution (e.g., improves the distribution) of the magnetic particles on the surface 384 of the sensor device 360.

The fluidic system 300 has a first surface 324a, second surface 324b and third surface 324c at the second end 380 of the fluid chamber 364. The first surface 324a, second surface 324b and third surface 324c are oriented at an angle $\beta_2$ relative to the surface 384 of the sensor device 360. The angled orientation of the first surface 324a, second surface 324b and third surface 324c relative to the surface 384 of the sensor device 360 causes fluid flow to change from the second flow direction (substantially in the positive X-Axis direction) to a third flow direction (substantially in the negative Y-Axis direction). Because the first surface 322a, second surface 322b and third surface 322c causes the flow to change from the first flow direction to the second flow direction, the flow (e.g., direction and velocity of the flow) is more uniform across the surface 384 of the sensor device 360 in the chamber 364 than the flow would otherwise be in the absence of the first surface 322a, second surface 322b and third surface 322c (e.g., flow across the surface 184 of the sensor device 160 in FIG. 1 is less uniform, volumetrically delivering less fresh sample across, and in proximity to, the sensor surface 184 in contrast to that achieved in embodiments of the invention).

In addition, in some embodiments, flow direction and velocity is more uniform near the center of the sensor device 360 (in both the Y-Axis and X-Axis) than at the edges of the sensor device 360 because turbulence or irregularity in the flow due to a change in the flow direction has had sufficient time to decrease or subside. In this embodiment, the second flow direction is substantially perpendicular to the third flow direction.

Assay results using fluidic systems produced according to principles of the present invention are dependent on the distribution of analyte, or microparticles carrying analyte, over the sensor surface (e.g., surface 384 of FIG. 3). Uniformly distributed sample flows over the sensor surface produces distributions of analyte (or microparticles carrying analyte) more uniform and consistent between assays. This results in improved assay coefficients of variation (CV's). In addition, fluidic systems produced according to principles of the present invention having desirable, uniform fluid flows over the sensor surface when distributing analyte (or microparticles carrying analyte) over the sensor surface, also provide desirable, uniform fluid flows over the sensor surface when washing off the analyte (or microparticles carrying analyte).

People that that conduct assays desire to use fluidic systems that produce repeatable results from one device (e.g., cartridge) to another. It is desirable for the fluidic systems to have fluid flow paths that are substantially the same from one device to another. This is difficult to achieve with prior art fluidic systems because of manufacturing tolerances which result in devices which vary in geometry. In addition, combining components of a fluidic system (e.g., wafer 306 and base 340 of FIG. 3A) results in misalignment of the components because of manufacturing/assembly tolerances. In some embodiments, the sensor devices (e.g., sensor device 360) can be manufactured with tolerances on the order of micrometers while the tolerances of molded plastic components are typically many 10's of micrometers. Embodiments of the present invention are able to produce repeatable assay results even though components of the fluidic system have such different tolerances.

In this embodiment, the first surface 324a, second surface 324b and third surface 324c are oriented at an oblique angle (i.e., an angle that is not a right angle or a multiple of a right angle). In some embodiments, the first surface 324a, second surface 324b and third surface 324c are curved surfaces and, therefore, the first surface 324a, second surface 324b and third surface 324c are oriented at an arcuate angle relative to the surface 384 of the sensor device 360.

Fluid flows through the fluid output 372 at the second end 380 of the fluid chamber 364. The fluid output 372 has a width of 397. As shown in FIG. 3A, in some embodiments, the second opening or fluid output 397 is arranged opposite the first surface 324a relative to the surface 384. The fluid output 372 is in fluidic communication with an output chamber 358 at the second end 380 of the chamber 364. The opening of the output chamber 358 (at the opposite end of the input chamber from the fluid output 372) has a width 393 and length 382. The cross-sectional area of the output chamber 356 increases as it departs from (in the negative Y-Axis direction) the fluid input 368. The output chamber 358 has a first section with a length 328 (along the Y-Axis) and width 393. The output chamber 358 has a second section with a length 326 (along the Y-Axis) and a width (along the X-Axis) that transitions from a width 393 to a width 372. The output chamber 358 has a third section with a length 328 (along the Y-Axis) with a width 372. The fluid flow then changes direction and flows along the fluid path 344 along the positive X-Axis direction. Fluid then flows out of a first output 354 of the cartridge 348 where it can be, for example, disposed.

In some embodiments, fluid flow properties are altered using one or more flow control devices (e.g., pumps, syringes or valves) to alter at least one of fluid pressure, flow rate or flow volume in the fluidic system. In some embodiments, altering fluid flow properties improves, for example, sensor device repeatability, insures that surfaces in the fluidic system are adequately wetted, or reduces gas bubbles in the fluidic system.

The wafer 306 includes a substrate 304, a membrane material 312 and a first material layer 310. The membrane material 312 is deposited on the wafer 304 using, for example, thin-film deposition techniques such as chemical or physical vapor deposition techniques. The membrane material 312 can be, for example, a silicon nitride material. The silicon nitride material has advantageous properties when used as a membrane material 312 and for wafer processing. For example, silicon nitride can be deposited over the substrate 304. Silicon nitride, particularly low-stress variations of silicon nitride, works well as a membrane material and as an etch mask during formation of the chamber 364. A separate mask layer (not shown) is, therefore, not required to be deposited or patterned on the substrate 304 prior to formation of the chamber 364. The pattern can be formed directly in the silicon nitride material.

The surfaces 322a, 322b, 322c are oriented at angle $\beta_1$ relative to the surface 384 of the sensor device 360 The surfaces 324a, 324b, 324c are oriented at angle $\beta_2$ relative to the surface 384 of the sensor device 360 The angles $\beta_1$ and $\beta_2$ are determined based on the type of removal process used to form the chamber 364 and the type of substrate material 304 (e.g., the lattice structure of the substrate material 304).

In alternative embodiments, the cartridge 348 is manufactured using a carrier substrate (or carrier chip) using semiconductor wafer processing techniques. In an alternative embodiment, straight slots are produced in the carrier substrate using a Deep Reactive Ion Etching process to produce walls similar to the walls 228 of FIG. 2, which are substantially vertical walls. Flow contraction and expansion features can be provided in the carrier substrate using an anisotropic etching process such as the process used to produce the sensor device cavity surfaces 322a, 322b, 322c and 322d. The processed carrier chip is combined with a sensor device layer to produce wafer 306. The wafer 306 is combined with a base 340 (e.g., a plastic base).

Various methods exist in the art for fabricating and assembling the components of a fluidic system. For example, various manufacturing processes (e.g., semiconductor manufacturing processes and injection molding processes) can be used to produce cartridges (and components of cartridges) in accordance with principles of the present invention. Exemplary fabrication and assembly methods are described in, for example, U.S. patent application Ser. No. 11/603,347, filed on Nov. 21, 2006 and entitled "Method and Apparatus for Analyte Processing"; the contents of which are hereby incorporated by reference.

Referring to FIGS. 3A, 3B and 3C, one embodiment of the invention was produced in which the width 388 of the input chamber 356 was about 406 micrometers; the width 395 of the input chamber 356 was about 254 micrometers; the width 393 of the output chamber 358 was about 406 micrometers; the width 397 of the output chamber 358 was about 254 micrometers; the length 382 of the input chamber 356 was about 1,219 micrometers; the depth 391 of the chamber 364 was about 508 micrometers; the length 320 of the sensor device 360 was about 1,600 micrometers; the width 386 of the sensor device 360 was about 400 micrometers; and the length 392 of the chamber 364 was about 2,300 micrometers.

In some embodiments, dimensions in the fluidic system are selected to provide desirable flow properties. In one embodiment, the ratio between the length 392 of the chamber 364 and the depth 391 of the chamber 364 is approximately 3-5. This ratio produces flow through the fluidic system 300 from the first input 350 to the first output 354 that is substantially different from a channel flow condition. Channel flows are typically characterized by flows through a channel having a length to depth ratio of 10 or greater.

In embodiments of the invention in which A) the ratio of length 392 of the chamber 364 to the width 395 of the input chamber 356 (and width 397 of the output chamber 358) is approximately 6, and B) the ratio of the depth 391 of the chamber 364 to the width 395 of the input chamber 356 (and width 397 of the output chamber 358) is approximately 2, fluid flows efficiently toward the surface 384 of the sensor device 360. In some embodiments, the ratio of the length 362 of the input chamber 356 to the width 395 of the input chamber 356 is greater than approximately 2 to allow for the flow to uniformly develop and speed up as the cross-sectional area contracts until the flow reaches the fluid input 368 at the first end 376 of the chamber 364. To further aide in turning the flow, the fluid input 368 and fluid output 372 are located at the ends (first end 376 and second end 380, respectively) of the chamber 364 such that the projection of the fluid input 368 and fluid output 372 on to an X-Z plane defined by the sensor device 360 does not overlap with the surface 384 of the sensor device 360.

Alternative embodiments of the invention can have different dimensions than those described above. For example, in some embodiments, the length 320 of the sensor device 360 is between about 1,200 micrometers and about 2,700 micrometers. In some embodiments, the length 320 of the sensor device 360 is less than 1,200 micrometers. In some embodiments, the length 320 of the sensor device 360 is greater than 2,700 micrometers. In some embodiments, the width 386 of the sensor device 360 is between about 300 micrometers and about 500 micrometers. In some embodiments, the width 386 of the sensor device 360 is less than 300 micrometers. In some embodiments, the width 386 of the sensor device 360 is greater than 500 micrometers. In some embodiments, the width 388 of the input chamber 356 is different than the width 393 of the output chamber 358. In some embodiments, the width 395 of the input chamber 356 is different than the width 397 of the output chamber 358. In some embodiments, the ratio of the width 388 of the input chamber 356 to the depth 391 of the chamber 364 was about 0.15. In some embodiments, the ratio of the length 382 of the input chamber 356 to the depth 391 of the chamber 364 was between about 3 and about 5.

In any of the above embodiments, a material layer, e.g., gold, can be deposited on the membrane and the walls of the chamber. This material layer facilitates the application of coatings that allow the surface properties to be modified for improved fluid flow through the chamber and along the membrane or for biofunctionalization of these surfaces. In some embodiments, a first material (not shown) is deposited on the chamber walls and a second, different material (not shown) is deposited on the membrane. Devices employing the concepts described above are suitable for a wide range of practical applications such as sensing, actuating, and pumping fluids. Properties and composition of the fluids can be determined based on the response of the frequency response of the device. Determining the presence or absence of chemical or biochemical components can be similarly determined. Furthermore, the amounts of these compounds can be quantified. Outputs of such systems include frequency responses and other signals capable of transmitting comparative information.

While the invention has been particularly shown and described with reference to specific embodiments, it should be understood by those skilled in the art that various changes in form and detail may be made therein without departing from the spirit and scope of the invention as defined by the appended claims.

What is claimed is:

1. A fluidic system, comprising:
a body structure defining a chamber disposed therein, wherein:
the chamber is defined by a first surface, a second surface, a first wall and a second wall,
the first surface and the second surface are opposing surfaces and extend from a first end of the chamber to a second end of the chamber,
the first surface is shorter than the second surface;
at least a portion of the first surface comprises a sensor device,
the first surface and a first end of the first wall join at the first end of the chamber, and
the first surface and a first end of the second wall join at the second end of the chamber;
at least one fluid input defined in the body structure at the first end of the chamber, the at least one fluid input defining a first opening between a second end of the first wall and a first end of the second surface;
at least one fluid output defined in the body structure at the second end of the chamber, the at least one fluid output defining a second opening between a second end of the second wall and a second end of the second surface;
wherein the first wall (i) includes a curved surface or (ii) is oriented at an angle that is not perpendicular or substantially perpendicular with respect to the first surface;
wherein the first opening is configured to direct fluid flowing from the at least one fluid input to the first wall, which directs the fluid along the first surface toward the second wall.

2. The fluidic system of claim 1, wherein the second wall (i) includes a second curved surface or (ii) is oriented at a second angle that is not perpendicular or substantially perpendicular with respect to the first surface, and wherein the fluid flowing from chamber to the at least one fluid output impinges on the second wall and is directed by the second wall through the second opening.

3. The fluidic system of claim 1, wherein the first opening is arranged opposite the first surface relative to the first wall.

4. The fluidic system of claim 1, wherein second opening is arranged opposite the first surface relative to the second wall.

5. The fluidic system of claim 1, comprising a removable source of magnetic flux located external to the chamber and close to the surface of the sensor device.

6. The fluidic system of claim 1, comprising an input chamber coupled to the at least one fluid input at the first end of the chamber, the input chamber cross-sectional area decreasing as it approaches the at least one fluid input.

7. The fluidic system of claim 1, comprising an output chamber coupled to the at least one fluid output at the second end of the chamber, the output chamber cross-sectional area increasing further away from the at least one fluid output.

8. The fluidic system of claim 1, wherein the sensor device is an acoustic device.

9. The fluidic system of claim 1, wherein a ratio between a length of the chamber and a depth of the chamber is about 3 to 5, thereby producing fluid flow through the chamber that is substantially different from channel flow.

10. The fluidic system of claim 5, wherein the magnetic flux close to the surface of the sensor device is selectively altered.

11. The fluidic system of claim 1, wherein the sensor device is a suspended membrane.

* * * * *